United States Patent
Yamaguchi et al.

(10) Patent No.: US 8,996,087 B2
(45) Date of Patent: Mar. 31, 2015

(54) BLOOD INFORMATION MEASURING METHOD AND APPARATUS

(75) Inventors: Hiroshi Yamaguchi, Kanagawa (JP); Takaaki Saito, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 202 days.

(21) Appl. No.: 13/436,179

(22) Filed: Mar. 30, 2012

(65) Prior Publication Data

US 2012/0253158 A1 Oct. 4, 2012

(30) Foreign Application Priority Data

Apr. 1, 2011 (JP) ................................. 2011-081755

(51) Int. Cl.
- *A61B 5/1455* (2006.01)
- *A61B 5/1459* (2006.01)
- *A61B 1/06* (2006.01)
- *A61B 5/06* (2006.01)

(52) U.S. Cl.
CPC .............. *A61B 5/1459* (2013.01); *A61B 1/0638* (2013.01); *A61B 5/065* (2013.01); *A61B 5/14551* (2013.01); *A61B 1/0646* (2013.01)
USPC ............ 600/322; 600/310; 600/323; 600/309

(58) Field of Classification Search
CPC ..................................................... A61B 5/1455
USPC .................................................. 600/310–344
See application file for complete search history.

(56) References Cited

U.S. PATENT DOCUMENTS

| | | | |
|---|---|---|---|
| 4,998,973 A | 3/1991 | Kikuchi | |
| 5,001,556 A | 3/1991 | Nakamura et al. | |
| 2006/0253036 A1 | 11/2006 | Takeuchi et al. | |
| 2008/0281154 A1 | 11/2008 | Gono et al. | |
| 2010/0036260 A1* | 2/2010 | Zuluaga et al. | 600/476 |
| 2010/0286475 A1* | 11/2010 | Robertson | 600/104 |

FOREIGN PATENT DOCUMENTS

| | | |
|---|---|---|
| EP | 1 774 897 A2 | 4/2007 |
| JP | 1-308531 A | 12/1989 |
| JP | 6-315477 A | 11/1994 |
| JP | 2000-262459 A | 9/2000 |
| JP | 2006-255323 A | 9/2006 |

* cited by examiner

*Primary Examiner* — Eric Winakur
*Assistant Examiner* — Marjan Fardanesh
(74) *Attorney, Agent, or Firm* — Birch, Stewart, Kolasch & Birch, LLP

(57) ABSTRACT

In a special mode, a superficial layer wavelength set, a middle layer wavelength set, and a deep layer wavelength set are selected successively. Each wavelength set is composed of 3 different types of narrowband light applied successively to an internal body portion. A wavelength set table specifies the number of repetitions of each wavelength set. A controller controls a wavelength band switching element to apply every type of the narrowband light of each wavelength set, and to apply each wavelength set for the number of repetitions specified by the wavelength set table. A CCD captures images of the internal body portion under illumination of the narrowband light of the respective wavelength sets. A blood information calculation section calculates oxygen saturation levels of hemoglobin in blood vessels in the superficial, middle, and deep layers based on image signals, respectively. This provides information on cancer progression.

16 Claims, 12 Drawing Sheets

| DEPTH | WAVELENGTH SET (nm) | NUMBER OF REPETITIONS PER CYCLE |
|---|---|---|
| SUPERFICIAL LAYER | 405, 445, 473 | 5 |
| MIDDLE LAYER | 540, 550, 580 | 1 |
| DEEP LAYER | 680, 805, 950 | 1 |

81

BLOOD INFORMATION MEASURING METHOD AND APPARATUS

BACKGROUND OF THE INVENTION

1. Field of the Invention

The present invention relates to a method and apparatus for measuring blood information based on an image signal of a blood vessel.

2. Description Related to the Prior Art

Endoscopes are widely used for observing lesions in subjects. The endoscope is provided with an insert section to be inserted into the subject and a handling section for operating the insert section. A distal end of the insert section is formed with a lighting window and an imaging window. An internal body portion is imaged under illumination. An observation image obtained is displayed on a monitor.

Generally, a white light source such as a xenon lamp or a metal halide lamp is used as a light source for the endoscope. Recently, it has become popular to use narrowband illumination light, which facilitates finding a lesion (see U.S. Patent Application Publication No. 2008/0281154 corresponding to Japanese Patent No. 3583731).

A method for measuring blood information, e.g. an oxygen saturation level or a blood flow rate, of blood in a blood vessel has been researched (see Japanese Patent Laid-Open Publication No. 06-315477). In this method, the blood vessel is extracted from an endoscopic image captured under illumination of narrowband light. The blood information is measured based on an image signal of the blood vessel. The method utilizes the narrowband illumination light in wavelength bands of 300 to 400 nm, around 400 nm, 400 to 500 nm, 500 to 600 nm, and 450 to 850 nm. For example, one of the above five wavelength bands most suitable for measuring the oxygen saturation level of hemoglobin is selected in accordance with the internal body portion. In the wavelength band selected, two different types of narrowband light are used as a wavelength set. One of the two types is measurement narrowband light that has a wavelength at which absorbance substantially varies with the oxygen saturation level. The other is reference narrowband light that has a wavelength at which the absorbance is unaffected. The two types of narrowband light are applied successively to the internal body portion. An image signal obtained from the measurement narrowband light is corrected using an image signal obtained from the reference narrowband light. Thereby, the oxygen saturation level of the blood in the blood vessel is obtained.

Depth of penetration of light into human tissue differs depending on the wavelength band. The wavelength sets of the illumination light are switched to measure the oxygen saturation level of blood in a blood vessel in each of the layers, from a mucosal layer to a deep layer. Thereby, a depth of invasion of a cancer lesion is detected.

The Japanese Patent Laid-Open Publication No. 06-315477 does not specifically disclose switching timing of the wavelength set. When the wavelength set is switched manually, a complicated operation is required, which is time-consuming. The internal body portion may move during the switching operation. On the other hand, when the wavelength set is switched automatically, the switching may take place during the observation of normal tissue. This results in unnecessary calculation of the oxygen saturation.

SUMMARY OF THE INVENTION

An object of the present invention is to provide a method and an apparatus for measuring blood information easily and appropriately.

To achieve the above and other objects of the present invention, a blood information measuring apparatus includes a lighting section, an imaging section, a wavelength band switching section, a wavelength band switching controller, and a blood information calculation section. The lighting section applies illumination light to an internal body portion including a blood vessel. The imaging section receives reflection light from the internal body portion illuminated with the illumination light, and outputs an image signal. The wavelength band switching section switches among wavelength bands of the illumination light to be applied to the internal body portion or of the reflection light to be incident on the imaging section such that two or more types of narrowband light constituting a designated wavelength set are applied or received successively. The two or more types penetrate to similar depths into the internal body portion. The wavelength band switching controller controls the wavelength band switching section to automatically and successively switch the designated wavelength set among the wavelength sets such that the application of the illumination light or the receipt of the reflection light of each of the wavelength sets is carried out for given number of repetitions. The blood information calculation section calculates blood information of blood in the blood vessel based on the image signal.

It is preferable that the blood information measuring apparatus further includes a monitor for displaying the blood information measured using each of the wavelength sets.

It is preferable that the lighting section includes a lighting window, and the lighting window and the imaging section are provided on an electronic endoscope.

It is preferable that the blood information is an oxygen saturation level of hemoglobin calculated based on absorbance.

It is preferable that at least one of the types of the narrowband light of the wavelength set causes a difference in absorption coefficient between oxyhemoglobin and deoxyhemoglobin. It is preferable that one of the types of the narrowband light of the wavelength set causes no difference in absorption coefficient between the oxyhemoglobin and the deoxyhemoglobin.

It is preferable that one of the wavelength sets is a superficial layer wavelength set having the types of narrowband light selected from within a blue wavelength band of 400 nm to 500 nm. In this case, it is preferable that two or more repetitions of application of the superficial layer wavelength set are carried out.

It is preferable that the blood information measuring apparatus further includes a location detecting section for detecting a location of the internal body portion. It is preferable that the number of repetitions of the application of the wavelength set is determined based on the location detected.

It is preferable that the location detecting section performs image processing to an image of the internal body portion to detect the location of the internal body portion.

It is preferable that the wavelength sets include a superficial layer wavelength set having the types of the narrowband light selected from within a blue wavelength band of 400 nm to 500 nm and a middle layer wavelength set having the types of the narrowband light selected from within a green wavelength band of 500 nm to 600 nm. It is preferable that the number of repetitions of the superficial layer wavelength set is set to two or more when the location detecting section detects that the internal body portion is esophagus or large intestine. It is preferable that the number of repetitions of the middle layer wavelength set is set to two or more when the location detecting section detects that the internal body portion is stomach.

It is preferable that the blood information measuring apparatus further includes an operation input section for changing a setting of number of repetitions of the application.

It is preferable that the lighting section applies white light of a broad wavelength band as the illumination light to the internal body portion. It is preferable that the wavelength band switching section is disposed in the lighting section to separate the narrowband light from the white light or in the imaging section to separate the narrowband light from the reflection light.

It is preferable that the monitor displays one of calculation results of the oxygen saturation levels obtained using the respective wavelength sets, or two or more of the calculation results side by side.

It is preferable that the wavelength sets include a deep layer wavelength set having the types of the narrowband light selected from within a red wavelength band of 600 nm to 1000 nm.

It is preferable that the blood information measuring apparatus further includes a mode selector for switching between a normal mode and a special mode. In the normal mode, an observation image is produced from the image signal obtained under illumination of white light of a broad wavelength band and displayed on the monitor. In the special mode, the wavelength sets are applied to calculate the oxygen saturation level and the oxygen saturation level is displayed on the monitor.

A blood information measuring method includes an illuminating step, an outputting step, a wavelength band switching step, a wavelength set switching step, and a calculating step. In the illuminating step, illumination light is applied to an internal body portion including a blood vessel. In the outputting step, reflection light is received from the internal body portion illuminated with the illumination light, and an image signal is outputted. In the wavelength band switching step, switching among wavelength bands of the illumination light to be applied to the internal body portion or of the reflection light is carried out such that two or more types of narrowband light constituting a designated wavelength set are applied or received successively. The two or more types of the narrowband light penetrate to similar depths into the internal body portion. In the wavelength set switching step, the designated wavelength set is automatically and successively switched among the wavelength sets such that the application of the illumination light or the receipt of the reflection light of each of the wavelength sets is carried out for given number of repetitions. In the calculating step, blood information of blood in the blood vessel is calculated based on the image signal.

It is preferable that the blood information measuring method further includes a step of displaying the blood information measured using each of the wavelength set.

It is preferable that the blood information is an oxygen saturation level of hemoglobin calculated based on absorbance.

According to the present invention, the wavelength sets are switched one after another after each of the wavelength sets is applied for the number of repetitions specified in accordance with the internal body portion to be observed. Thereby, the switching among the wavelength sets is carried out easily and appropriately. This facilitates measurement of the blood information in the depth direction of the tissue.

BRIEF DESCRIPTION OF THE DRAWINGS

The above and other objects and advantages of the present invention will be more apparent from the following detailed description of the preferred embodiments when read in connection with the accompanied drawings, wherein like reference numerals designate like or corresponding parts throughout the several views, and wherein.

DESCRIPTION OF THE PREFERRED EMBODIMENTS

Figure 1:
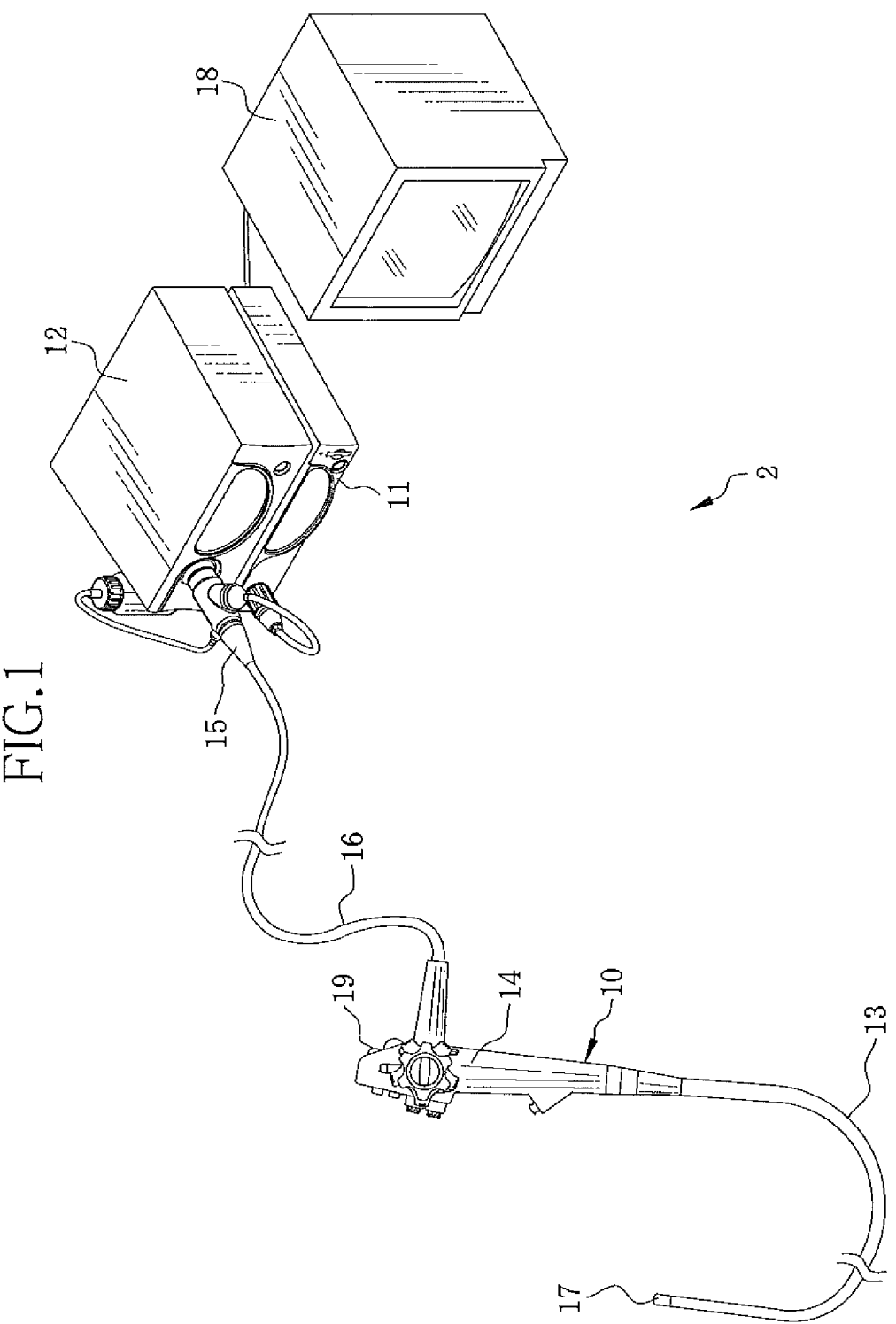
FIG. 1 is an external view of a blood information measuring apparatus.

In FIG. 1, a blood information measuring apparatus 2 is composed of an electronic endoscope 10, a processor device 11, a light source device 12, and the like. The electronic endoscope 10 has, as is well known, a flexible insert section 13 to be inserted into a subject (patient), a handling section 14 joined to a basal portion of the insert section 13, a connector 15 connected to each of the processor device 11 and the light source device 12, and a universal cord 16 connecting the handling section 14 to the connector 15. Note that this blood information measuring apparatus 2 is similar to a well-known electronic endoscope system except that an image processor and a CPU of the processor device 11 have additional functions for measuring blood information.

The handling section 14 is provided with operation members, for example, an angle knob for bending a distal portion 17 of the insert section 13 in horizontal and vertical directions, an air/water button for ejecting air and/or water from an air/water nozzle, and a release button for capturing a still observation image (endoscopic image).

A forceps inlet is provided on a distal side of the handling section 14. A medical instrument such as an electric scalpel is inserted into the forceps inlet. The forceps inlet is connected to a forceps outlet provided on the distal portion 17 through a forceps channel in the insert section 13.

The processor device 11 is connected electrically to the light source device 12 through a cable and controls operation of the whole blood information measuring apparatus 2. The processor device 11 supplies power to the electronic endoscope 10 through a transmission cable routed through the universal cord 16 and the insert section 13. The processor device 11 controls operation of a CCD (see FIG. 2) in the distal portion 17. The processor device 11 receives an image signal outputted from the CCD 33 through the transmission cable. The processor device 11 performs various image processing steps to the image signal to produce image data. The image data is sent to a monitor 18 and displayed as an observation image on the monitor 18 cable-connected to the processor device 11.

The blood information measuring apparatus 2 is provided with a normal mode and a special mode. In the normal mode, an internal body portion of the subject is observed under illumination with white light. In the special mode, narrow-band light is applied to the internal body portion to calculate blood information. A mode switch 19 on the handling section 14 is used for switching between modes. When turned on, the blood information measuring apparatus 2 is automatically set to the normal mode by a command from the processor device 11.

Figure 2:
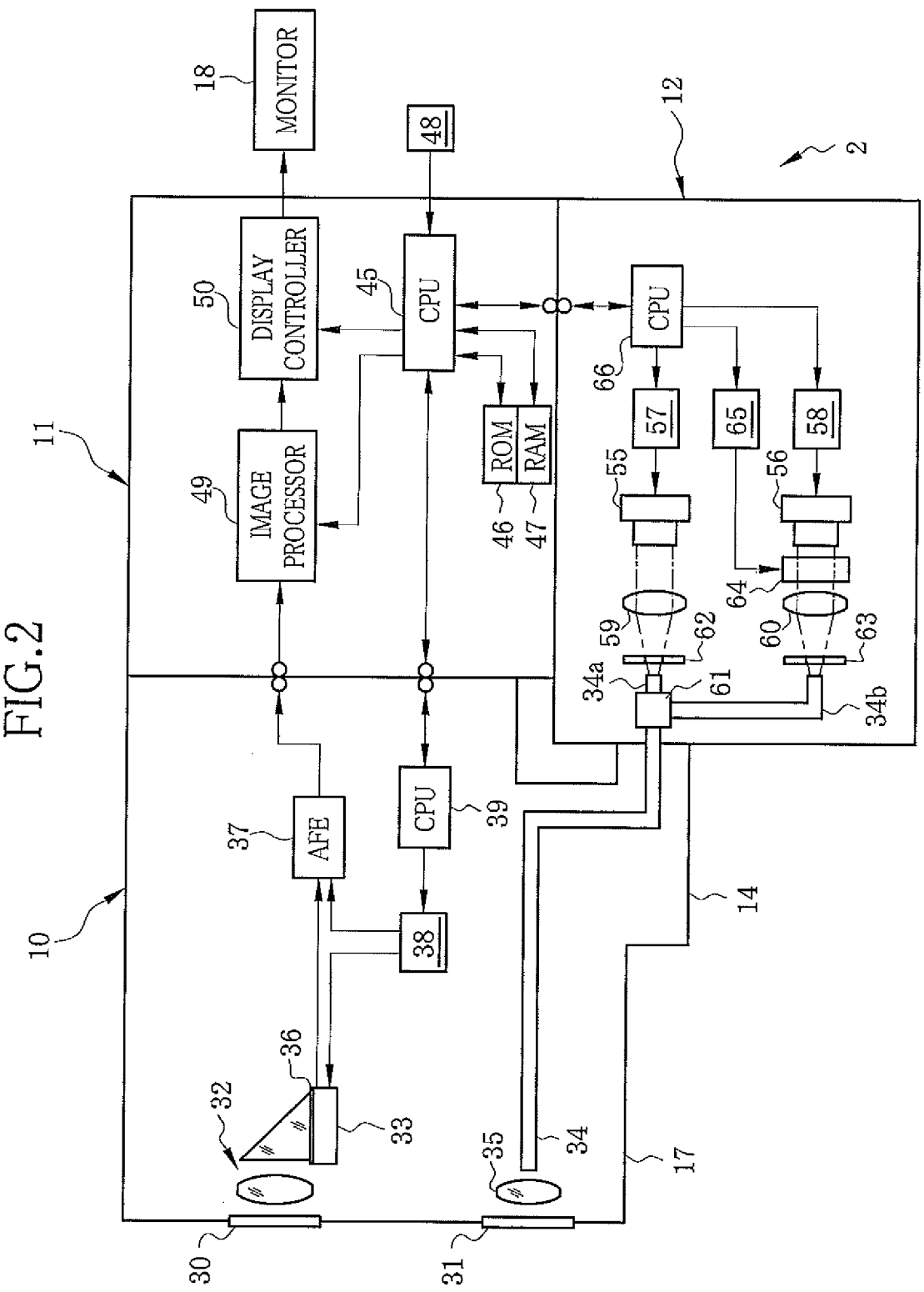
FIG. 2 is a block diagram of the blood information measuring apparatus.

In FIG. 2, an imaging window 30, a lighting window 31, and the like are provided on a distal end surface of the distal portion 17. Behind the imaging window 30, an objective optical system 32 composed of a lens group and a prism is disposed. A CCD 33 is disposed behind the objective optical system 32. The illumination light from the light source device 12 is applied to the internal body portion from the lighting window 31 through a light guide 34 and a lighting lens 35.

Figure 3:
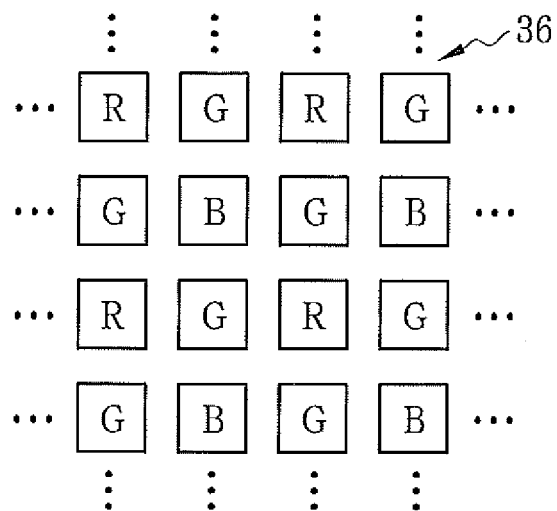
FIG. 3 is an explanatory view of a color filter with a Bayer arrangement.
Figure 4:
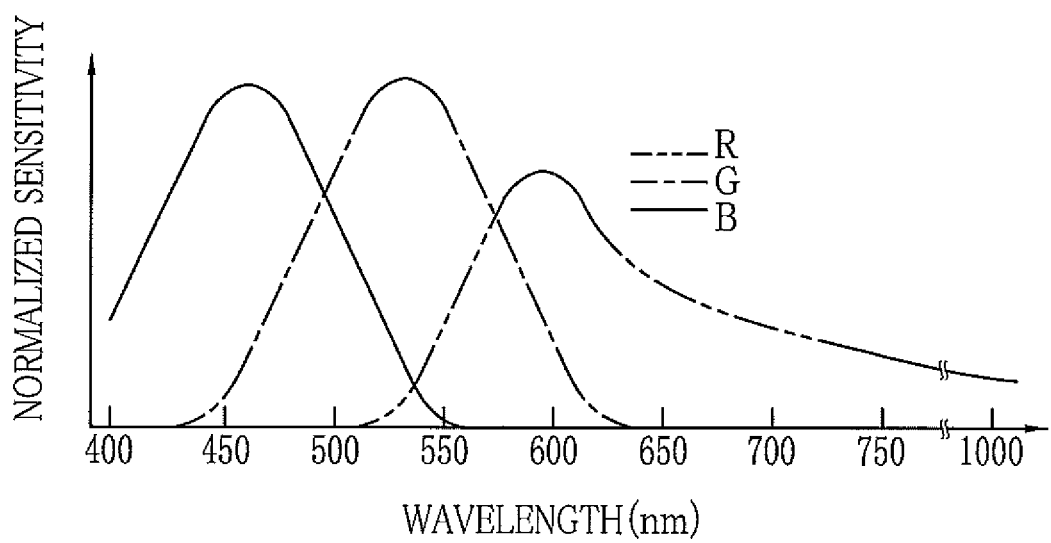
FIG. 4 is a graph showing spectral sensitivity characteristics of each of R, G, and B pixels of a CCD.

Reflection light from the internal body portion is incident on the CCD 33 through the imaging window 30 and the objective optical system 32. The CCD 33 converts the reflection light photoelectrically into the image signal and outputs the image signal. A color filter, e.g. a primary color filter 36, composed of multiple color segments is formed on an imaging surface of the CCD 33. The primary color filter 36 has, for example, a Bayer arrangement (R: red, G: green, and B: blue) as shown in FIG. 3. FIG. 4 shows spectral sensitivity characteristics of each of the R, G, and B pixels of the CCD 33, determined by spectral transmittance of the primary color filter 36 and the spectral sensitivity of pixels themselves. The R pixel has a sensitivity peak at around 600 nm. The G pixel has a sensitivity peak at around 530 nm. The B pixel has a sensitivity peak at around 460 nm. The R pixel has a wide range of spectral sensitivity and detects light even including an infrared region at around 1000 nm.

An analog front end (AFE) 37 is composed of a correlated double sampling circuit (CDS), an automatic gain controller (AGC), and an analog/digital converter (A/D), as is well known. The CDS performs correlated double sampling to the image signal outputted from the CCD 33, to remove reset noise and amplification noise occurred in the CCD 33. Then the AGC amplifies the image signal with a gain specified by the processor device 11. Thereafter, the A/D converts the image signal into a digital image signal of a predetermined bit number. The digital image signal is inputted to an image processor 49 of the processor device 11 through a transmission cable.

A CCD driver 38 generates drive pulses (vertical/horizontal scan pulses, electronic shutter pulse, read-out pulse, reset pulse, and the like) for the CCD 33 and a synchronization pulse for the AFE 37. In response to the drive pulse from the CCD driver 38, the CCD 33 carries out imaging operations to output an image signal. Each section of the AFE 37 operates in response to the synchronization pulse from the CCD driver 38.

After the electronic endoscope 10 is connected to the processor device 11, a CPU 39 actuates the CCD driver 38 in response to an operation start command from a CPU 45 of the processor device 11. The CPU 39 adjusts the gain of the AGC in the AFE 37 through the CCD driver 38.

The CPU 45 controls the operation of the whole processor device 11. The CPU 45 is connected to each section through a data bus, an address bus, and control lines (all not shown). A ROM 46 stores various programs (OS, application programs, and the like) for controlling the operation of the processor device 11, and data (graphic data, and the like). The CPU 45 reads out the necessary programs and the data from the ROM 46 and loads them into a RAM 47 being a working memory, and runs the programs in sequence. The CPU 45 obtains information, such as text data including examination date and time, a patient's name, and a doctor's name, on an examination-by-examination basis from an operation panel of the processor device 11 or through a network, for example, LAN (local Area Network), and writes the information to the RAM 47.

An operation unit 48 is a well-known input device such as the operation panel provided on a housing of the processor device 11, a mouse, or a keyboard. The CPU 45 operates each section in response to an operation signal from the operation unit 48 or from a release button or the mode switch 19 provided on the handling section 14 of the electronic endoscope 10.

The image processor 49 performs various image processing steps such as color interpolation, white balance adjustment, gamma correction, image enhancement, image noise reduction, and color conversion to the image signal inputted from the electronic endoscope 10. The image processor 49 calculates blood information which will be described later.

A display controller 50 receives the graphic data from the ROM 46 and the RAM 47 through the CPU 45. The graphic data includes a display mask, text data, and a graphical user interface (GUI). The display mask covers an ineffective pixel area of the observation image to display only an effective pixel area. The text data includes the examination date and time, the patient's name, the doctor's name, and the current mode selected. The display controller 50 performs various display control processing steps to the image sent from the image processor 49. The display control processing steps include superimposition of the display mask, the text data, and the GUI on the image, and a drawing process for displaying the image on a screen of the monitor 18.

The display controller 50 has a frame memory (not shown) for temporarily storing the image from the image processor 49. The display controller 50 reads out the image from the frame memory and then converts the image into a video signal (component signal, composite signal, or the like) conforming to a display format of the monitor 18. Thereby, an observation image is displayed on the monitor 18.

In addition, the processor device 11 is provided with a compression circuit, a media I/F, a network I/F, and the like (all not shown). The compression circuit compresses the image with a predetermined compression format (for example, a JPEG format). The media I/F writes the compressed image to a removable medium such as a CF card, a magneto-optical disk (MO), or a CD-R. The network I/F controls transmission of various types of data to and from a network such as the LAN. The compression circuit, the media I/F, the network I/F, and the like are connected to the CPU 45 through the data bus and the like.

The light source device 12 has a first light source 55 and a second light source 56. The first and second light sources 55 and 56 have the same structure. Each of the first and second light sources 55 and 56 is, a xenon lamp, a halogen lamp, or a white LED (light emitting diode) that emits white light of a broad wavelength band, for example, of 400 nm (blue region)

to 1000 nm (red region). Alternatively, each of the first and second light sources 55 and 56 may be another light source which emits the white light. For example, the white light is generated by mixing blue or ultraviolet excitation light emitted from a semiconductor laser and fluorescence, ranging in color from green to yellow to red, emitted from a phosphor by the excitation.

The first and second light sources 55 and 56 are driven by light source drivers 57 and 58, respectively. Condenser lenses 59 and 60 gather light from the first and second light sources 55 and 56 to allow the light to be incident on light guides 34a and 34b, respectively. The light guides 34a and 34b are disposed on exit end sides of the first and second light sources 55 and 56, respectively. The light guides 34a and 34b are connected to a single light guide 34 through a coupler 61. A variable aperture stop 62 is disposed between the condenser lens 59 and the light guide 34a. A variable aperture stop 63 is disposed between the condenser lens 60 and the light guide 34b. The variable aperture stops 62 and 63 control light quantities of the light incident on the light guides 34a and 34b, respectively. Instead of the coupler 61, the first and second light sources 55 and 56 may be provided with their respective light guides to transmit the light separately to the lighting window 31.

A wavelength band switching element 64 is disposed between the second light source 56 and the condenser lens 60. The wavelength band switching element 64 is driven by an element driver 65. The wavelength band switching element 64 switches among wavelength bands of light to be transmitted therethrough. Examples of the wavelength band switching elements 64 include an etalon and a liquid crystal tunable filter. The etalon has two highly reflecting filters. An actuator such as a piezoelectric element is used for changing a space between the two filters so as to control the wavelength band of the light to be transmitted. The liquid crystal tunable filter has a birefringent filter and a nematic liquid crystal cell sandwiched between polarizing filters. A voltage applied to the liquid crystal cell is changed to control the wavelength band of the transmission light. Alternatively, a rotary filter being a combination of interference filters (bandpass filters) may be used as the wavelength band switching element 64.

A CPU 66 of the light source device 12 communicates with the CPU 45 of the processor device 11. The CPU 66 separately controls ON/OFF of the first light source 55 through the light source driver 57 and that of the second light source 56 through the light source driver 58. The CPU 66 separately controls the light quantity of the first light source 55 through the variable aperture stop 62 and that of the second light source 56 through the variable aperture stop 63. The CPU 66 controls the wavelength band switching element 64 through the element driver 65.

When the normal mode is selected, the CPU 45 controls the light source driver 57 through the CPU 66 to turn on only the first light source 55, namely, only the white light is applied to the internal body portion. When the special mode is selected, the CPU 45 allows the light source driver 57 to turn off the first light source 55 and turn on the second light source 56, namely, only narrowband light separated by the wavelength band switching element 64 is applied to the internal body portion.

Figure 5:
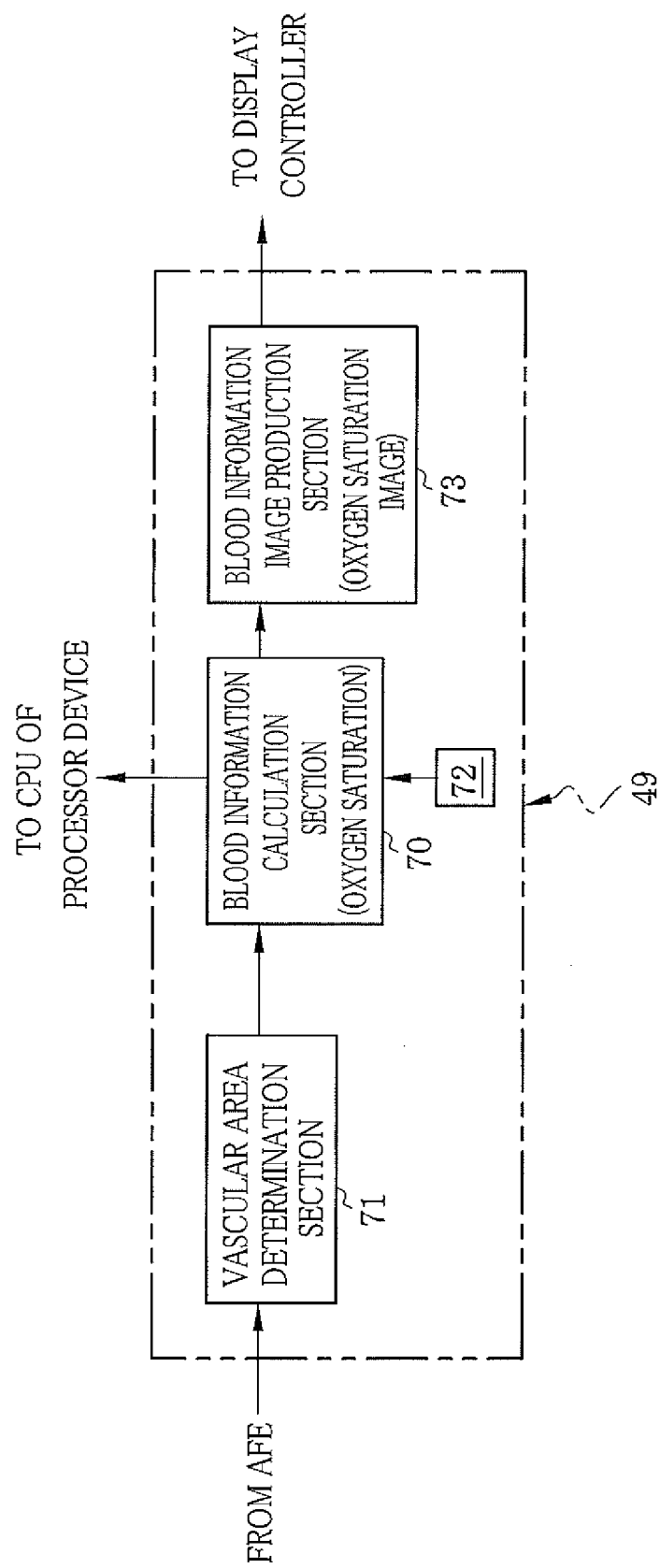
FIG. 5 is a block diagram of an image processor.

In FIG. 5, the image processor 49 is provided with a vascular area determination section 71, a blood information calculation section 70, and a blood information image production section 73. The vascular area determination section 71 analyzes an image inputted from the AFE 37. For example, the vascular area determination section 71 obtains or refers to a difference in luminance value between a vascular area and a non-vascular area to determine (extract) the vascular area in (from) the image. The blood information calculation section 70 calculates the blood information from the image signal of the vascular area determined. Examples of the blood information include an oxygen saturation level of hemoglobin, a blood flow rate, and a blood vessel depth. In this embodiment, measurement of the oxygen saturation level of hemoglobin is described by way of example.

Figure 6:
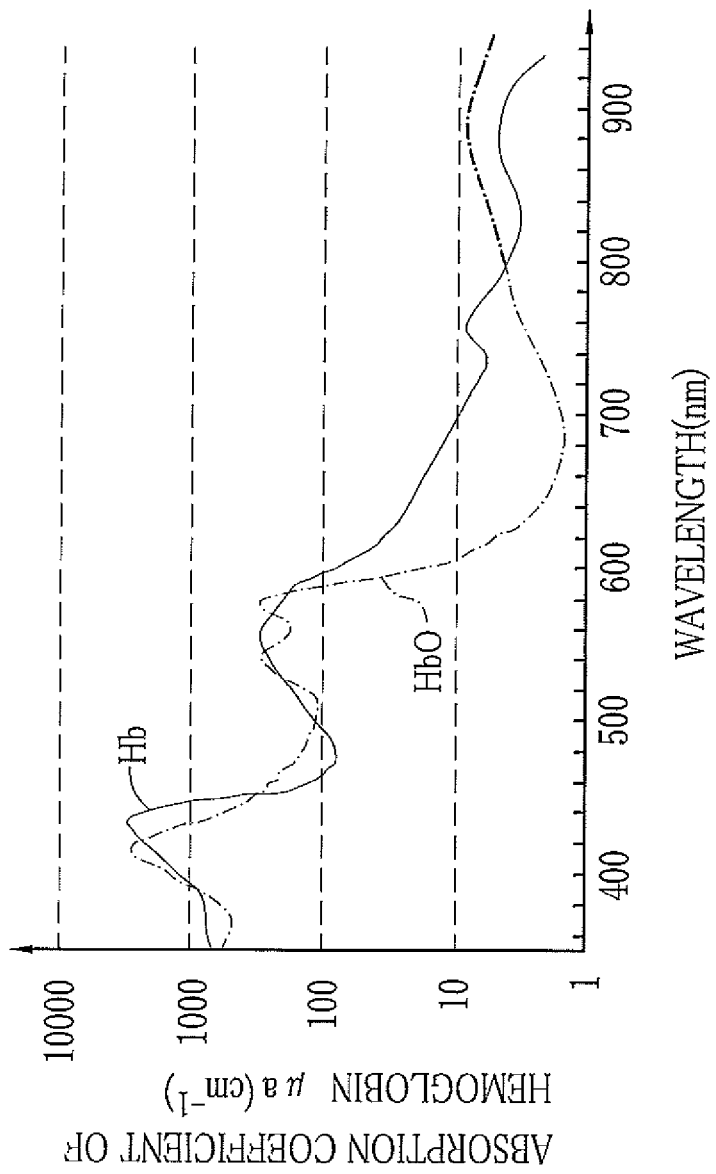
FIG. 6 is a graph showing absorption characteristics of oxyhemoglobin and deoxyhemoglobin.

As shown in FIG. 6, an absorption coefficient $\mu a$ of the hemoglobin varies with a wavelength of the illumination light. The absorption coefficient $\mu a$ refers to magnitude (absorbance) of light absorbed by the hemoglobin. The absorption coefficient is a coefficient of an expression $I_0 \exp(-\mu a x x)$ representing attenuation of the light applied to the hemoglobin. Note that "$I_0$" denotes intensity of the illumination light, and "x" (unit: cm) denotes a depth of the blood vessel from the surface of the internal body portion.

Deoxyhemoglobin Hb not combined with oxygen differs from oxyhemoglobin HbO combined with the oxygen in light absorption properties. An absorption coefficient $\mu a$ of the deoxyhemoglobin is different from that of the oxyhemoglobin except at isosbestic points. The isosbestic point is a point of intersection of the absorption coefficients $\mu a$ of the deoxyhemoglobin and oxyhemoglobin, at which the absorption coefficients $\mu a$ of the deoxyhemoglobin and the oxyhemoglobin have the same value.

When there is a difference in absorption coefficient $\mu a$ between the deoxyhemoglobin and the oxyhemoglobin, intensities of the reflection light from the blood vessel vary even if light of a constant wavelength and constant intensity is applied to the blood vessel. When light of different wavelengths and constant intensity is applied to the blood vessel, the intensities of the reflection light still vary because the absorption coefficient $\mu a$ varies with the wavelength. Accordingly, a ratio between the oxyhemoglobin and the deoxyhemoglobin in the blood vessel, that is, the information of the oxygen saturation level is obtained or determined by analyzing images captured under the illumination of the two or more types of narrowband light.

The blood information calculation section 70 has a frame memory (not shown) for temporarily storing the images captured under the illumination of the respective types of narrowband light. The blood information calculation section 70 reads out each image from the frame memory. The blood information calculation section 70 uses the image signal of the vascular area, determined by the vascular area determination section 71, of each image to carry out various calculations. For example, the blood information calculation section 70 calculates a ratio or a difference between the image signals (pixel values) of the same color between frames to obtain an image parameter, e.g. absorbance. To be more specific, for example, when the oxygen saturation level is calculated using first to third frames G1 to G3, captured under the illumination of respective first to third types of narrowband light, the blood information calculation section 70 calculates "G1/G3" and "G2/G3" as the image parameters. In this embodiment, a combination or a set of the first to third types of the narrowband light is referred to as the wavelength set. The first to third types of the narrowband light penetrate to similar depths. Two or more wavelength sets are used based on their respective depths of penetration into the internal body portion. Generally, the depth of penetration increases at longer wavelengths.

Figure 7:
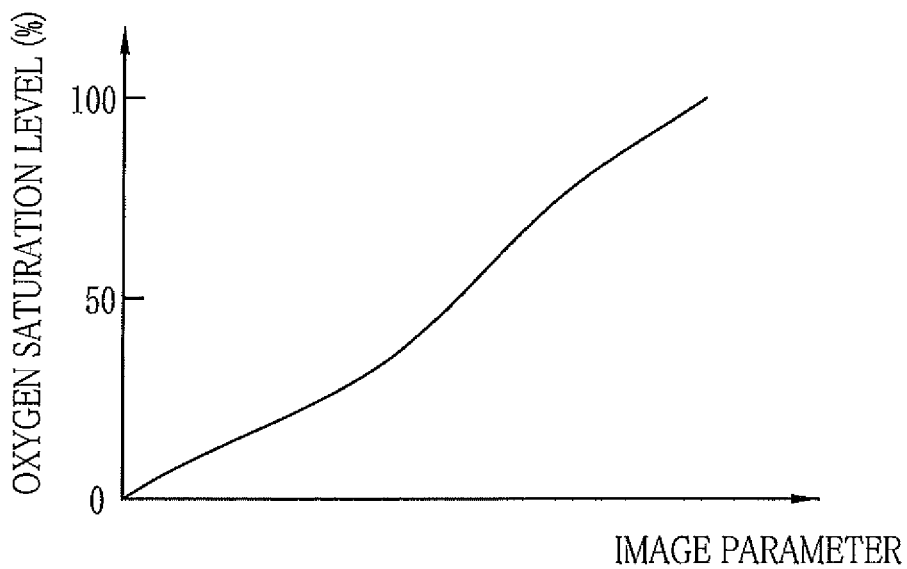
FIG. 7 is a graph of an example of reference data.

As shown in FIG. 7, reference data 72 shows relation between the image parameter and the oxygen saturation level in a form of a function or a data table on an individual wavelength set basis. The relation between the image parameter and the oxygen saturation level is determined in advance by experiments or the like. The blood information calculation section 70 obtains the oxygen saturation level corresponding to the image parameter from the reference data 72. For example, the blood information calculation section 70 substitutes the image parameter into the function to calculate the oxygen saturation level corresponding to the image parameter, or retrieves the oxygen saturation level corresponding to the image parameter from the data table. The calculation result of the oxygen saturation level is outputted to each of the blood information image production section 73 and the CPU 45.

Based on a color map, the blood information image production section 73 produces an oxygen saturation image reflecting or representing the calculation result of the blood information calculation section 70. The color map is used for displaying the calculation result in pseudo color. A numerical value of the oxygen saturation level, obtained by the blood information calculation section 70 with the use of the reference data 72, is displayed as text data on the oxygen saturation image. The color map assigns cyan to a relatively low oxygen saturation level, magenta to a medium oxygen saturation level, and yellow to a high oxygen saturation level, for example.

Figure 8:
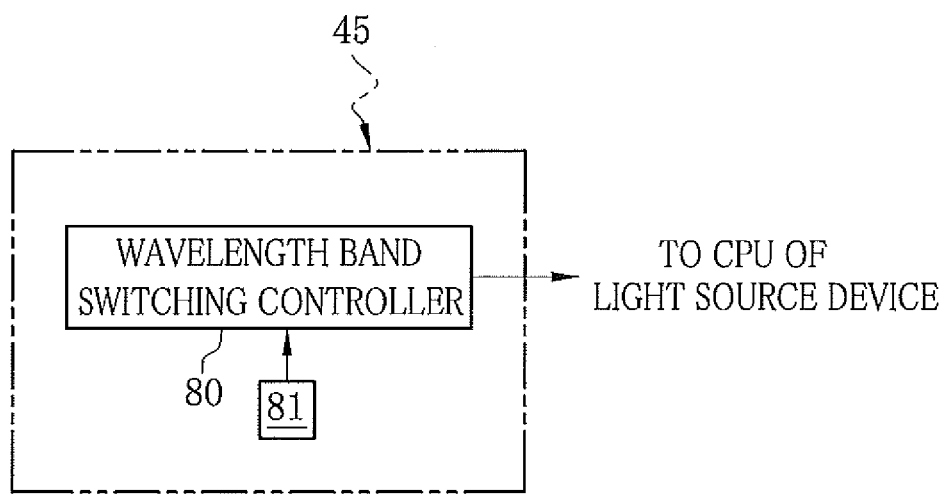
FIG. 8 is a block diagram of a CPU of a processor device.
Figures 9, 10:
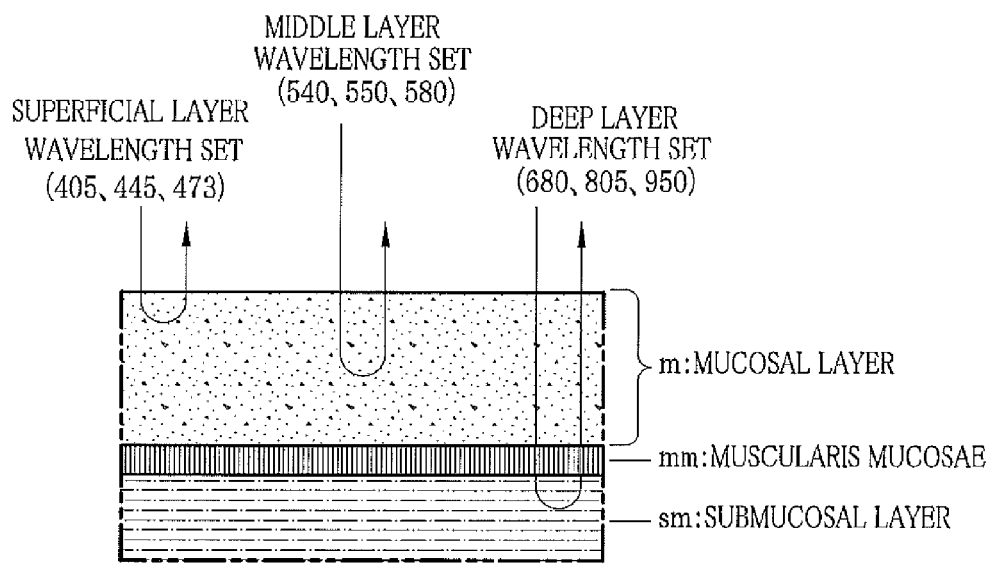
FIG. 9 is an example of a wavelength set table.
FIG. 10 is an explanatory view of depths of penetration of illumination light of each wavelength set.

As shown in FIG. 8, running the program in the ROM 46 allows the CPU 45 to function as a wavelength band switching controller 80. The wavelength band switching controller 80 selects or designates a wavelength set of the narrowband light from a wavelength set table 81 (shown in FIG. 9) stored in the ROM 46. The wavelength set table 81 has optimum wavelength sets for calculating the oxygen saturation levels of the blood vessels in the respective superficial, middle, and deep layers, and the number of repetitions of the application of each wavelength set. The data in the wavelength set table 81 is stored in advance. Each wavelength set includes, for example, a wavelength band at which the absorption coefficient μa of the deoxyhemoglobin is different from that of the oxyhemoglobin, and a wavelength band (corresponding to the isosbestic point) at which the deoxyhemoglobin and oxyhemoglobin have the same absorption coefficient μa. The narrowband light of these wavelength bands penetrate to similar or the substantially the same depths. The wavelength set for the superficial layer (hereinafter referred to as the superficial layer wavelength set) includes 405 nm corresponding to the isosbestic point, 445 nm, and 473 nm, selected from within a wavelength band of 400 nm to 500 nm. The wavelength set for the deep layer (hereinafter referred to as the deep layer wavelength set) includes 680 nm, 805 nm corresponding to the isosbestic point, and 950 nm (near infrared light), selected from within the wavelength band of 600 nm to 1000 nm. The wavelength set for the middle layer (hereinafter referred to as the middle layer wavelength set) includes 540 nm, 550 nm, and 580 nm, selected from within the wavelength band of 500 nm to 600 nm. These wavelengths are emission peaks of the narrowband light. As shown in FIG. 10, the light of the superficial layer wavelength set reaches a depth of several tens μm from the surface of the mucosal layer. The light of the middle layer wavelength set reaches a depth from several tens to several hundreds μm, which is deeper than that of the light of the superficial layer wavelength set. The light of the deep layer wavelength set reaches from the muscularis mucosae to the submucosal layer. Note that in this embodiment, each wavelength set includes 3 wavelengths by way of example. Each wavelength set may include 2 or more than 3 wavelengths.

The wavelength set table 81 specifies the number of repetitions of the application of each wavelength set required per cycle. In each cycle, each of the superficial layer wavelength set, the middle layer wavelength set, and the deep layer wavelength set is applied to the internal body portion for the number of repetitions specified, to calculate the respective oxygen saturation levels. In this embodiment, the number of required repetitions of the application of the superficial layer wavelength set is "5". The number of required repetitions of the application of the middle layer wavelength set is "1" (meaning that the middle layer wavelength set is applied once), and the number of required repetitions of the application of the deep layer wavelength set is "1" (meaning that the deep layer wavelength set is applied once). The wavelength band switching controller 80 outputs a signal to the CPU 66 of the light source device 12 to allow the light source device 12 to apply each wavelength set for the number of repetitions specified.

Figure 11:
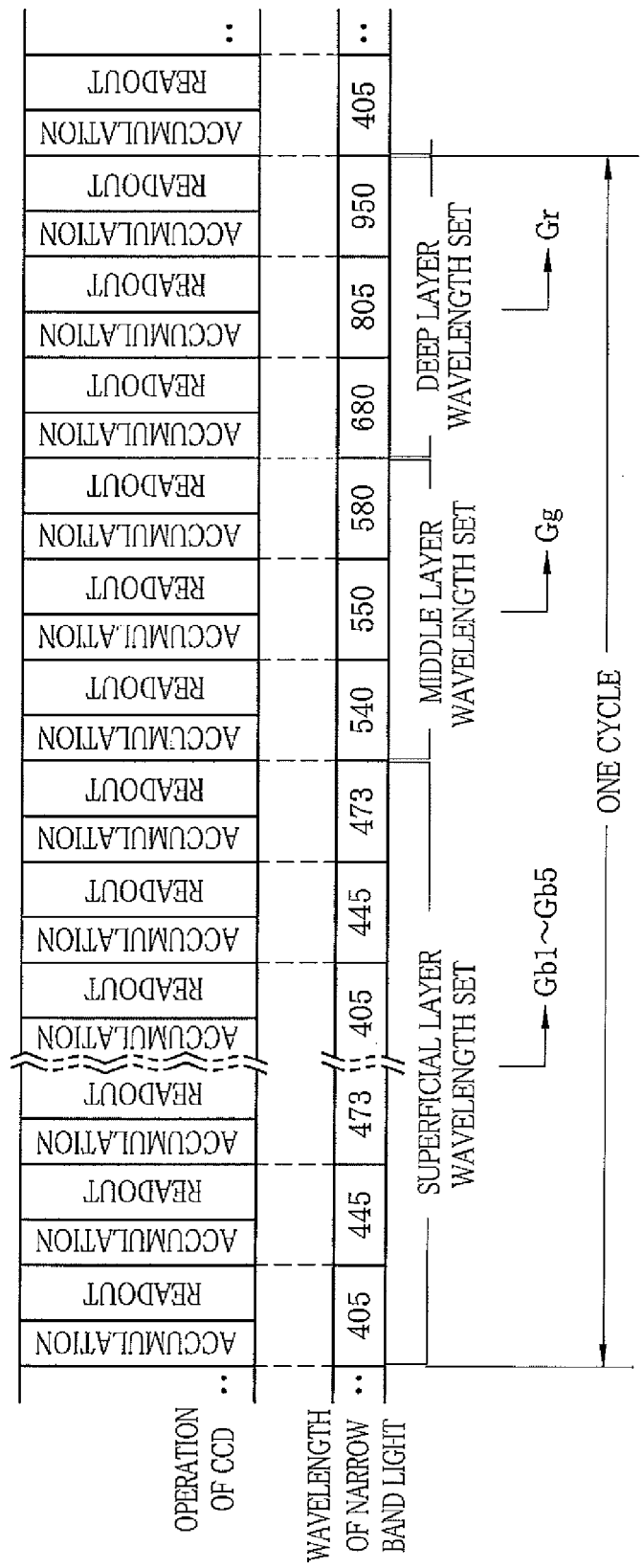
FIG. 11 is a timing chart showing switching among the wavelength sets.

As shown in FIG. 11, when the special mode is selected using the mode switch 19, the wavelength band switching controller 80 initially selects the superficial layer wavelength set. The CPU 66 of the light source device 12 controls the wavelength band switching element 64 such that the light of each wavelength of the superficial layer wavelength set is applied to the internal body portion for a unit of an accumulation period of the CCD 33, one after another. The 5 successive repetitions of the application of the superficial layer wavelength set are carried out as specified by the wavelength set table 81. Thereafter, to the CPU 66, the wavelength band switching controller 80 outputs the signal to switch from the superficial layer wavelength set to the middle layer wavelength set and then to switch from the middle layer wavelength set to the deep layer wavelength set. The CPU 66 controls the wavelength band switching element 64 to apply the narrowband light of each wavelength of the middle layer wavelength set to the internal body portion for a unit of the accumulation period of the CCD 33, one after another. Then, the narrowband light of each wavelength of the deep layer wavelength set is applied to the internal body portion for a unit of the accumulation period of the CCD 33, one after another. Thereby, one cycle is carried out, namely, every wavelength set is applied. After the application of the deep layer wavelength set, the application of the superficial layer wavelength set is carried out.

The order of the middle layer wavelength set and the deep layer wavelength set may be interchanged. Instead of the 5 successive repetitions of the superficial layer wavelength set, the middle and deep layer wavelength sets may be applied somewhere between the repetitions of the superficial layer wavelength set. For example, after 2 successive repetitions of the superficial layer wavelength set, the middle layer wavelength set is applied once, and then the 2 successive repetitions of the superficial layer wavelength set are carried out. Thereafter, the deep layer wavelength set is applied once, and then finally the superficial layer wavelength set is applied once. The order of the wavelength sets can be interchanged freely as long as the number of repetitions, specified by the wavelength set table 81, of every wavelength set is carried out. When the 5 successive repetitions of the superficial layer wavelength set are carried out, there is a time lag between the first application of the superficial layer wavelength set and each of the applications of the middle and deep layer wavelength sets. On the other hand, when the middle and deep layer wavelength sets are applied somewhere between the repetitions of the superficial layer wavelength set, concurrency in calculations of the oxygen saturation levels based on the respective wavelength sets is ensured.

Each of oxygen saturation images Gb1 to Gb5, Gg, and Gr carries information on the oxygen saturation level in the thickness (depth) direction. The oxygen saturation images Gb1 to Gb5 are obtained from the respective 5 repetitions of the application of superficial layer wavelength set. The oxygen saturation image Gg is obtained from the single application of the middle layer wavelength set. The oxygen saturation image Gr is obtained from the single application of the deep layer wavelength set. The display controller 50 displays one of the oxygen saturation images Gb1 to Gb5, Gg, and Gr at a time, or two or more of the oxygen saturation images side by side. The display may be switched between a single image and multiple images manually or automatically at regular intervals. This facilitates comparison between the oxygen saturation images and thus the diagnosis is carried out without difficulty.

In response to the operation of the release button, the CPU 45 writes the oxygen saturation images Gb1 to Gb5, Gg, and Gr, obtained in one cycle, to the ROM 46 or a removable medium. The oxygen saturation images Gb1 to Gb5, Gg, and Gr are associated with one another.

As is well known, in progression (including metastasis and invasion) of a cancer, cancer tissue produces a growth factor (vascular endothelial growth factor, VEGF) to compensate for the shortage of oxygen (blood flow). The growth factor promotes angiogenesis or growth of neovessels (new blood vessels) from pre-existing vessels. Thereby, a new vascular network is formed to increase the blood flow to the lesion so as to alleviate hypoxic condition. The neovessels grow downward from peripheral portions of the cancer tissue, to be connected to relatively broad vessels in the submucosal layer. Although the cancer tissue itself is in a relatively low oxygen saturation level, a portion with the neovessels surrounding the cancer tissue is in a relatively high oxygen saturation level.

Figure 12A:
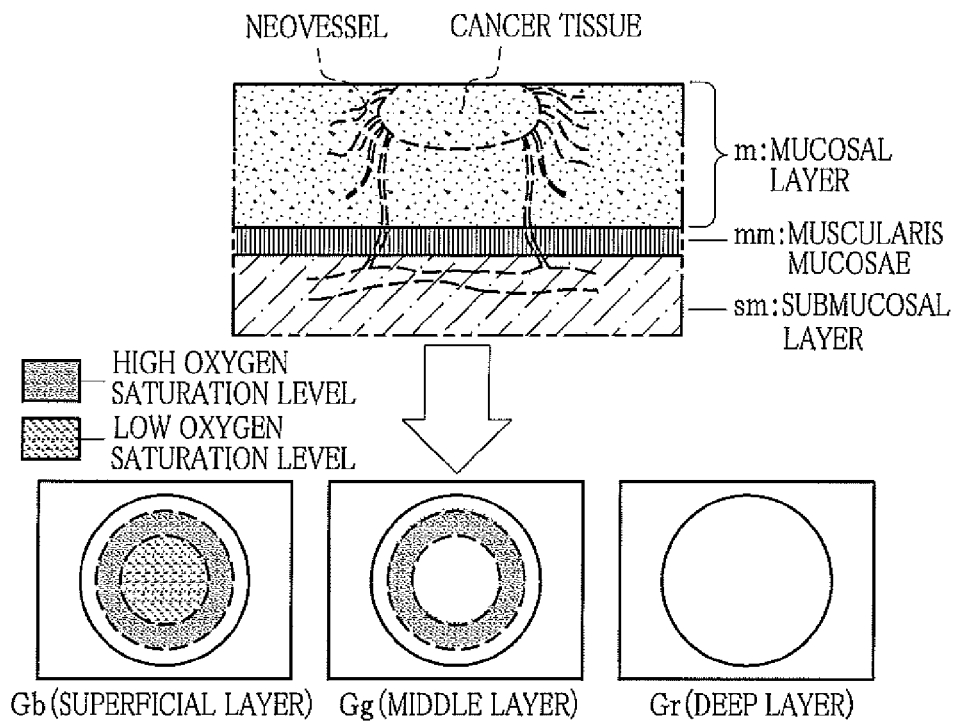
FIG. 12A is an explanatory view showing examples of oxygen saturation images of early cancer captured using respective wavelength sets.

As shown in FIG. 12A, when the cancer is in its early stage (early cancer), that is, when the cancer tissue remains within the mucosal layer above the muscularis mucosae, the neovessels grow from the mucosal layer to the middle layer so as to surround the cancer tissue. The oxygen saturation image Gb shows a central region (low oxygen saturation region) with a low oxygen saturation level and an annular region (high oxygen saturation region) with high oxygen saturation level. The low oxygen saturation region corresponds to the cancer tissue. The high oxygen saturation region corresponds to the neovessels. On the other hand, the oxygen saturation image Gg captured with the application of the middle layer wavelength set only has the annular high oxygen saturation region corresponding to the neovessels and does not have the low oxygen saturation region corresponding to the cancer tissue. An oxygen saturation image Gr captured with the application of the deep layer wavelength set does not show a difference in oxygen saturation level.

Figure 12B:
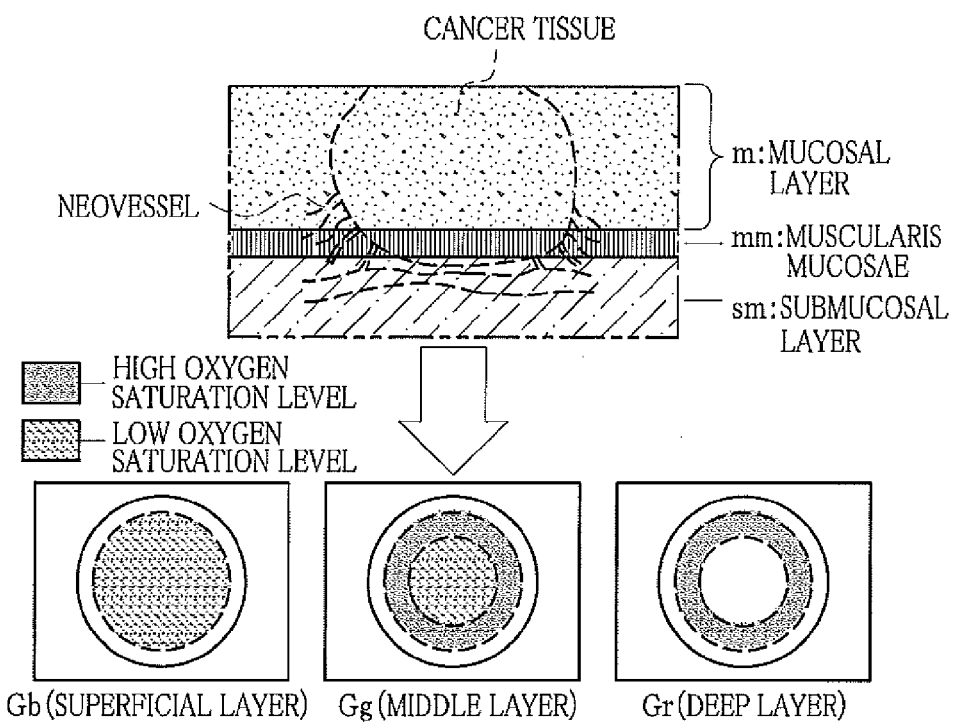
FIG. 12B is an explanatory view showing examples of oxygen saturation images of advanced cancer captured using the wavelength sets.

On the other hand, as shown in FIG. 12B, when the cancer tissue is an advanced caner reaching the submucosal layer through the muscularis mucosae, the oxygen saturation image Gb is mostly the low oxygen saturation region corresponding to the cancer tissue. On the other hand, the oxygen saturation image Gg shows, similar to the oxygen saturation image Gb in FIG. 12A, the central low oxygen saturation region corresponding to the cancer tissue and the annular high oxygen saturation region corresponding to the neovessels. The oxygen saturation Gr only shows the annular high oxygen saturation region corresponding to the neovessels.

Accordingly, the oxygen saturation levels shown in the oxygen saturation images Gb, Gg, and Gr differ depending on the progression of the cancer. By analyzing a pattern of the high and low oxygen saturation levels in each of the oxygen saturation images Gb, Gg, and Or, cancer staging (depth of invasion) is determined.

Figure 13:
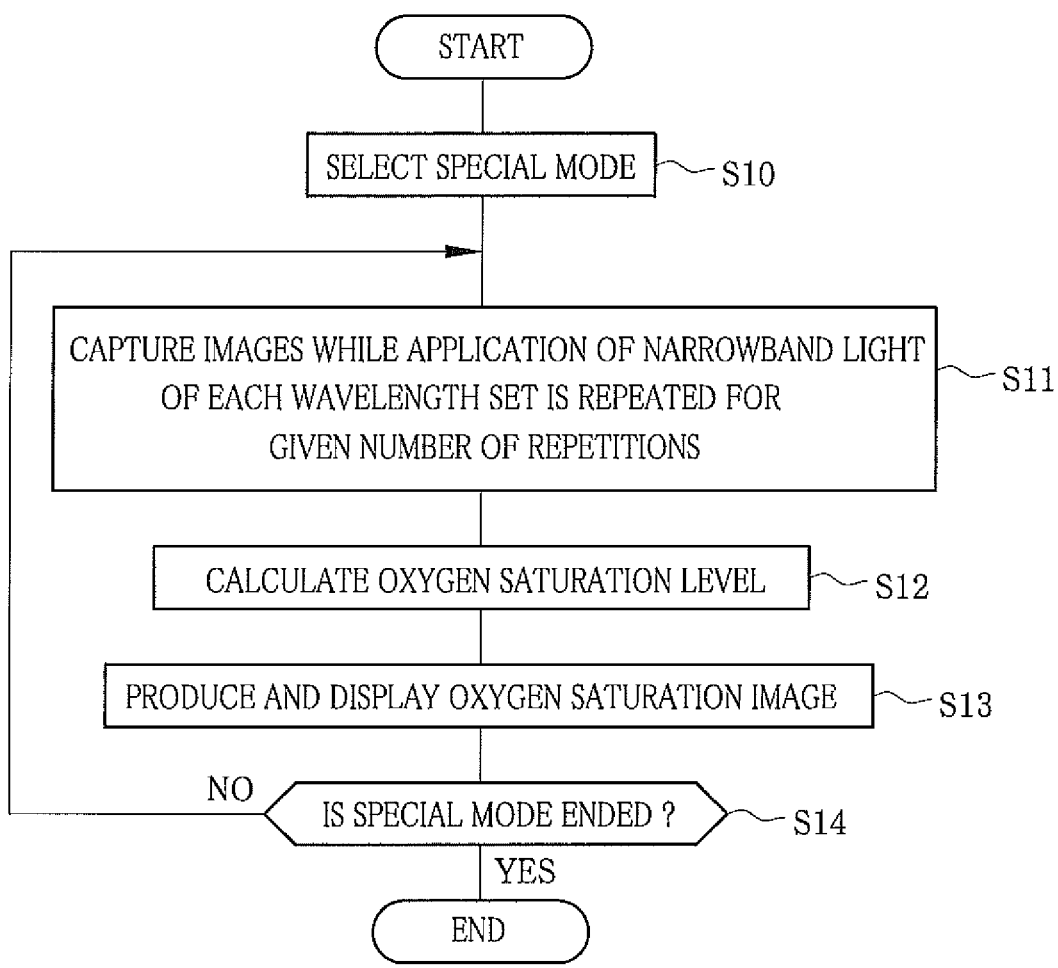
FIG. 13 is a flowchart showing a procedure in a special mode.

Next, referring to FIG. 13, an operation of the blood information measuring apparatus 2 is described. Patient information is inputted and the start of the examination is commanded using the operation unit 48. Then the insert section 13 of the electronic endoscope 10 is inserted into the subject. Under the illumination of the illumination light from the light source device 12, an observation image of the internal body portion is captured with the CCD 33. The observation image is displayed on the monitor 18.

To be more specific, the image signal outputted from the CCD 33 is subjected to various processing steps in each section of the AFE 37. Then, the image signal is inputted to the image processor 49. The image processor 49 performs various image processing steps to the image signal to produce the image of the internal body portion. The image is inputted to the display controller 50. The display controller 50 performs various display control processing steps in accordance with the graphic data. Thereby, the observation image is displayed on the monitor 18.

When the insert section 13 of the electronic endoscope 10 is inserted into the subject, a normal mode is selected to illuminate the internal body portion with the white light. Thereby, a wide view is ensured while the insert section 13 is inserted. When a lesion requiring careful observation is found and it is necessary to obtain its oxygen saturation level, the special mode is selected. In the special mode, the oxygen saturation image is captured under the illumination of the narrowband light of a wavelength suitable for the lesion and observed. When necessary, a still image of the lesion is captured with the operation of a release button provided on the electronic endoscope 10. When a treatment is needed, a medical instrument is inserted into the forceps channel of the electric endoscope 10 to remove the lesion or give medicine to the lesion.

In the normal mode, in response to the command of the CPU 45, the CPU 66 turns on the first light source 55 to apply the white light to the internal body portion through the lighting window 31.

On the other hand, as shown in S10 of FIG. 13, when the special mode is selected using the mode switch 19, the wavelength band switching controller 80 selects the superficial layer wavelength set. The CPU 66 turns off the first light source 55 and turns on the second light source 56. The CPU 66 controls the wavelength band switching element 64 such that the narrowband light of each wavelength of the superficial layer wavelength set is applied to the internal body portion for the unit of the accumulation period of the CCD 33, successively. The 5 successive repetitions of the application of the superficial layer wavelength set are carried out. The CCD 33 captures the reflection light of each application of the superficial layer wavelength set. Then, to the CPU 66, the wavelength band switching controller 80 outputs a signal to switch from the superficial layer wavelength set to the middle layer wavelength set, and then to switch from the middle layer wavelength set to the deep layer wavelength set. The CPU 66 controls the wavelength band switching element 64 to allow the application of the middle layer wavelength set once and then the application of the deep layer wavelength set once. The narrowband light of each wavelength of the middle wavelength set is applied to the internal body portion for the unit of the accumulation period of the CCD 33, successively. Then, the narrowband light of each wavelength of the deep wavelength set is applied to the internal body portion for the unit of the accumulation period of the CCD 33, successively. The CCD 33 captures the reflection light of each of the applications of the middle and deep layer wavelength sets in order (S11).

In the image processor 49, first, the vascular area determination section 71 determines the vascular area. Then, based on the reference data 72, the blood information calculation section 70 calculates the oxygen saturation level of hemoglobin in the blood vessel (S12). Thereafter, the blood information image production section 73 produces the oxygen saturation images Gb1 to Gb5 captured using the superficial layer wavelength set, the oxygen saturation image Gg captured using the middle layer wavelength set, and the oxygen saturation image Gr captured using the deep layer wavelength set. One or more of the oxygen saturation images are displayed at a time on the monitor 18 (S13). The oxygen saturation images may be displayed side by side. When the release button is operated, the oxygen saturation images Gb1 to Gb5, Gg, and Gr of one cycle are associated with one another and written to the ROM 46 or a removable medium. After the application of the narrowband light of the deep layer wavelength set, the application of the narrowband light of the superficial layer wavelength set is carried out (back to S11). The above-described steps are repeated until the special mode is ended (YES in S14), for example, when the normal mode is selected using the mode switch 19.

As described above, in the present invention, the superficial layer, the middle layer, and the deep layer wavelength sets are automatically switched one after another when the number of repetitions of the application specified by the wavelength set table 81 is carried out. The narrowband light of each wavelength set is applied to the internal body portion to calculate the oxygen saturation level. Thus, the blood information (oxygen saturation level) in the depth direction from the surface of the mucosal layer to the deep layer, which is useful in determining the cancer staging, is obtained easily.

A capillary near the surface of the mucosal layer is observed under the illumination of the narrowband light of the superficial layer wavelength set. The size of the capillary is extremely small, for example, of the order of 10 μm. This degrades the reliability of the oxygen saturation level of the capillary obtained using the superficial layer wavelength set, when compared with that of middle layer vessel (of the order of 50 μm) obtained using the middle layer wavelength set and that of the deep layer vessel (of the order of 100 μm) obtained using the deep layer wavelength set. For this reason, in this embodiment, the number of repetitions of the superficial layer wavelength set is set to "5" to obtain the oxygen saturation images Gb1 to Gb5. Thereby, reproducibility of the calculation results of the oxygen saturation level is checked by comparison between the oxygen saturation images Gb1 to Gb5. In other words, the reproducibility is ensured when all the oxygen saturation images Gb1 to Gb5 appear to be substantially the same. Note that the calculation result is determined as unreliable when it is different from the rest of the calculation results by more than a predetermined value. Such calculation result may be eliminated so as not to be displayed on the monitor 18 and not to be written to the ROM 46.

Chronological changes in the oxygen saturation images Gb, Gg, and Gr between examinations of a patient show a rate of cancer progression. This is useful in distinguishing undifferentiated carcinoma, which grows rapidly after metastasis.

A method for diagnosing cancer tissue has been established, which uses an image of a capillary in a superficial layer captured under the illumination of the narrowband light. Accordingly, the calculation of the oxygen saturation level of the capillary in the superficial layer particularly attracts attention. To meet the need for more accurate calculation, the number of repetitions of the superficial layer wavelength set is set greater than those of the middle and deep layer wavelength sets in this embodiment. When the internal body portion to be observed is in esophagus or large intestine, it is preferable to increase the number of repetitions of the superficial layer wavelength set as in this embodiment.

Conversely, the number of repetitions of the middle layer wavelength set may be increased. Although the hypoxic region (cancer tissue) in the mucosal layer can be detected using the superficial layer wavelength set, it is difficult to find scirrhous gastric cancer because the surface of its lesion is covered with normal tissue or the normal tissue remains in the lesion. On the other hand, the middle layer wavelength set is suitable for the calculation of the oxygen saturation level of hemoglobin in a relatively broad blood vessel in the middle layer of the mucosa. Accordingly, the increased number of repetitions of the middle layer wavelength set ensures finding the scirrhous gastric cancer with the hypoxic region not evident in the mucosal layer.

Figure 14:
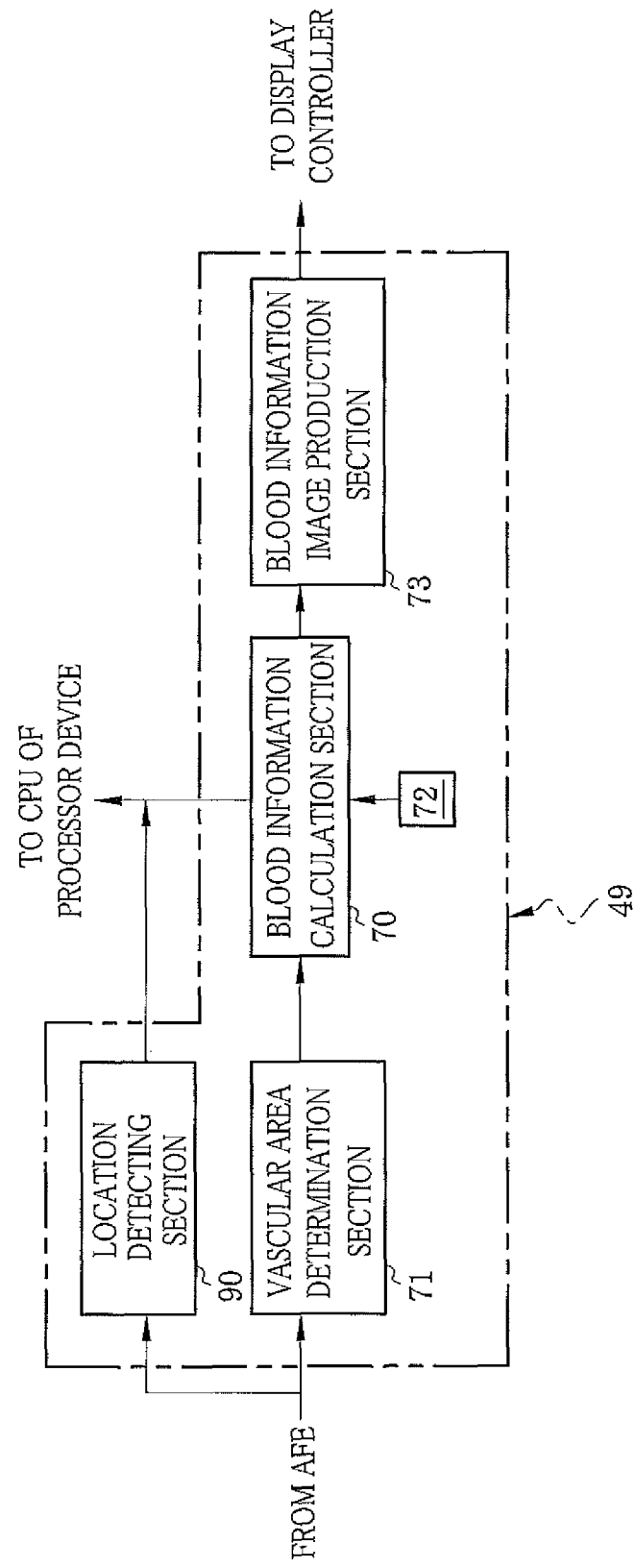
FIG. 14 is a block diagram of an image processor of a second embodiment.

Instead of fixing the number of repetitions of each wavelength set, the number of repetitions may be varied in accordance with an internal body portion to be observed. For example, when an upper gastrointestinal tract endoscope is used, the number of repetitions of the superficial layer wavelength set is increased to observe esophagus. On the other hand, in the observation of stomach, the number of repetitions of the middle layer wavelength set is increased to find scirrhous gastric cancer with high reliability. To vary the number of repetitions of the wavelength set, the handling section 14 of the electronic endoscope 10 may be provided with an operation member for changing the setting manually, for example. Alternatively, as shown in FIG. 14, the image processor 49 may include a location detecting section 90. The location detecting section 90 uses a well-known image recognition technique to detect or recognize whether the internal body portion being observed is in the esophagus or the stomach, for example. The number of repetitions of the wavelength set may be changed automatically based on the recognition result.

The image recognition technique includes a pattern recognition method using the location detecting section 90, for example, pattern recognition of cardia that is a junction with a unique shape between the esophagus and the stomach. In another method, a dark area in the image is compared with a threshold value because the dark area in the image of esophagus is small before the endoscope passes through the cardia though the dark area in the image of stomach is large. Any methods can be employed as long as the internal body portion being observed is recognized or identified. For example, an image of a patient being examined can be captured using CT scan to detect the position of the distal portion 17 of the electronic endoscope 10 inside the patient's body. Alternatively, the distal portion 17 may be provided with a pH sensor to identify the internal body portion being observed based on pH differences.

When the number of repetitions of the middle layer wavelength set is increased to "5", for example, the number of repetitions of the superficial layer wavelength set may be changed to "1" in the above embodiment. Alternatively, for example, the number of repetitions of the middle layer wavelength set is changed to "5" while the number of repetitions of the superficial layer wavelength set is unchanged ("5" in the above embodiment).

The reliability of the calculation results of the oxygen saturation level increases as the number of the repetitions of the wavelength sets increases. However, too many repetitions prolong the total imaging time required per cycle. This causes time lags in capturing the oxygen saturation images Gb, Gg, and Gr, resulting in loss of concurrency. It is preferable that the number of repetitions of each wavelength set per cycle is determined based on a balance between the reliability of the calculation result of the oxygen saturation level and the concurrency.

Figure 15:
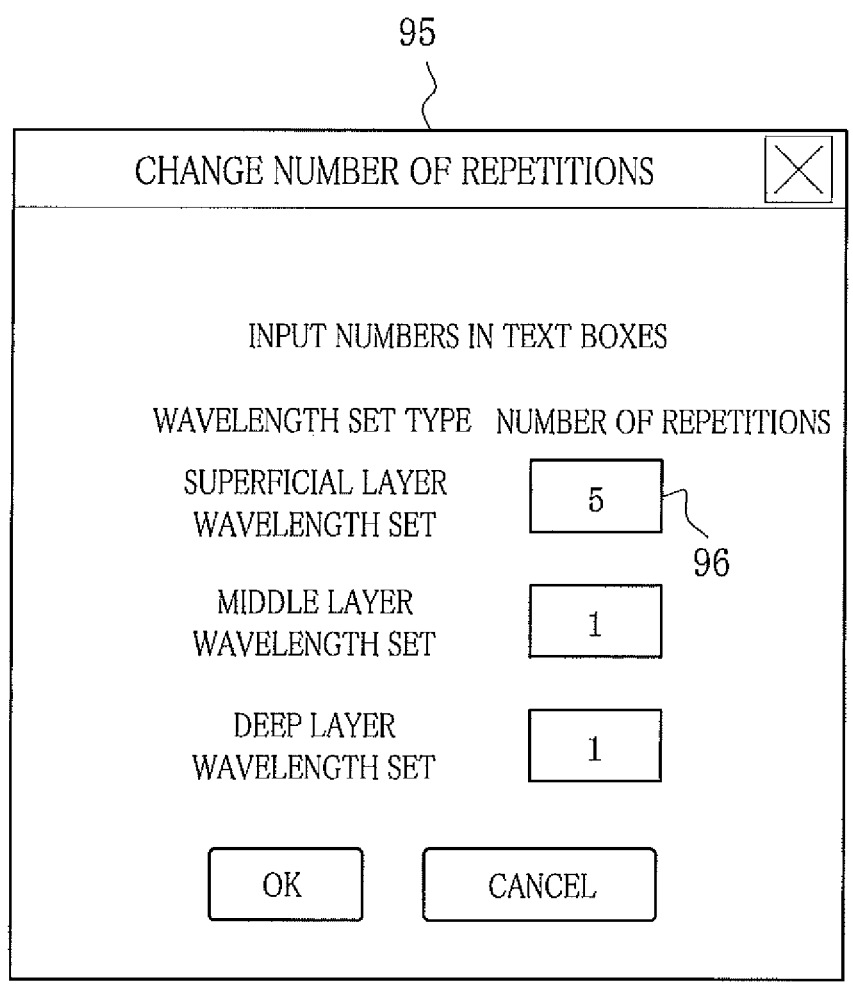
FIG. 15 is an example of a setting window displayed on a monitor screen.

Note that, a setting window 95 shown in FIG. 15 may be displayed on the monitor 18 to change the number of repetitions of the application of each wavelength set, with the use of the operation unit 48. The setting window 95 has text boxes 96. The text box 96 is selected and the number of repetitions is inputted thereto. The number of repetitions is changed by selecting an OK button. An operation button for returning to a default setting may be provided. This enables calculation of the oxygen saturation level with the number of repetitions varied with the internal body portion to be observed.

The reliability of the calculation result of the oxygen saturation level may decrease due to insufficient resolution of the image of the capillary when unmagnified observation is carried out with the electronic endoscope 10 having zoom function or when there is more than a predetermined distance between the distal portion 17 and the internal body portion. In these cases, the number of repetitions of the superficial layer wavelength set may be set to "2" or more to increase the reliability of the calculation result of the oxygen saturation level.

The wavelength sets in the wavelength set table 81 in FIG. 9 are shown by way of example. Instead of or in addition, wavelength sets with different combinations of wavelengths may be used. For example, wavelength sets suitable for the respective segments (superficial, middle, and deep segments or layers) of the mucosal layer may be used.

The application of each wavelength set may be carried out once. The cycle of application may not be repeated. The application of every wavelength set may be carried out for only one cycle.

The special mode may include various modes, for example, a mode for obtaining vascular images (visible images of blood flow in vessels) of the superficial, middle, and deep layers using the narrowband light of respective wavelengths (450 nm, 550 nm, 780 nm, and the like), a mode for injecting a fluorescent substance to living tissue and observing fluorescence, generated by excitation, from the internal body portion, and a mode for observing intrinsic fluorescence of living tissue.

In the above embodiment, the wavelength band switching element 64 is disposed between the second light source 56 and the light guide 34b. The wavelength band switching element 64 may be disposed on the exit end side of the light guide 34. The wavelength band switching element 64 may be provided on the objective optical system for taking an image of the internal body portion, for example, behind the imaging window 30 or on the imaging surface of the CCD 33. Instead of the wavelength band switching element, light sources for emitting the narrowband light of the respective different wavelength bands may be provided.

In the above embodiment, the oxygen saturation level of the hemoglobin is obtained from the absorbance or concentration being a logarithm of the absorbance. Alternatively, the blood flow rate may be obtained as the blood information from the absorbance or the like. The size of the region from which the oxygen saturation is calculated may be a microscopic spot instead of the size corresponding to the imaging area of the CCD.

The electronic endoscope is used in the above embodiment. Instead, an endoscope of a different type may be used, for example, a fiberscope with an image guide or an ultrasonic endoscope incorporating an image sensor and an ultrasonic transducer at its tip. The present invention is also applicable to a system which does not use an endoscope. In this case, the narrowband light is applied to a patient's body surface to obtain blood information of a blood vessel near the body surface. The insert section is unnecessary in this system.

Various changes and modifications are possible in the present invention and may be understood to be within the present invention.

What is claimed is:

1. A blood information measuring apparatus comprising:
    a lighting section for applying illumination light to an internal body portion including a blood vessel;
    an imaging section for receiving reflection light from the internal body portion illuminated with the illumination light, and outputting an image signal;
    a wavelength band switching section for switching among wavelength bands of the illumination light to be applied to the internal body portion or of the reflection light to be incident on the imaging section such that two or more types of narrowband light constituting a designated wavelength set are applied or received successively, the two or more types of the narrowband light penetrating to similar depths into the internal body portion;
    a memory storing a wavelength set table in which the wavelength sets and the number of repetitions of the application of each wavelength set are stored, the number of repetitions of the application of at least one of the wavelength sets being two or more, and a combination of the number of repetitions of the application of each wavelength set being different according to a location of the internal body portion;
    a wavelength band switching controller for controlling the wavelength band switching section to automatically and successively switch the designated wavelength set among the wavelength sets such that the application of the illumination light or the receipt of the reflection light of each of the wavelength sets is carried out for the number of repetitions stored in the wavelength set table;
    a location detecting section for detecting a location of the internal body portion, wherein the combination of the number of repetitions of application of each of the wavelength sets is determined automatically based on the location detected, and
    a blood information calculation section for calculating blood information of blood in the blood vessel based on the image signal.

2. The blood information measuring apparatus of claim 1, further including a monitor for displaying the blood information measured using each of the wavelength sets.

3. The blood information measuring apparatus of claim 2, wherein the lighting section includes a lighting window, and the lighting window and the imaging section are provided on an electronic endoscope.

4. The blood information measuring apparatus of claim 3, wherein the blood information is an oxygen saturation level of hemoglobin calculated based on absorbance.

5. The blood information measuring apparatus of claim 4, wherein at least one of the types of the narrowband light of the wavelength set causes a difference in absorption coefficient between oxyhemoglobin and deoxyhemoglobin and one of the types of the narrowband light of the wavelength set causes no difference in the absorption coefficient between the oxyhemoglobin and the deoxyhemoglobin.

6. The blood information measuring apparatus of claim 4, wherein one of the wavelength sets is a superficial layer wavelength set having the types of narrowband light selected from within a blue wavelength band of 400 nm to 500 nm, and two or more repetitions of application of the superficial layer wavelength set are carried out.

7. The blood information measuring apparatus of claim 6, further including an operation input section for changing a setting of the number of repetitions.

8. The blood information measuring apparatus of claim 4, wherein the lighting section applies white light of a broad wavelength band as the illumination light to the internal body portion, and the wavelength band switching section is disposed in the lighting section to separate the narrowband light from the white light or in the imaging section to separate the narrowband light from the reflection light.

9. The blood information measuring apparatus of claim 4, wherein the monitor displays one of calculation results of the oxygen saturation levels obtained using the respective wavelength sets, or two or more of the calculation results side by side.

10. The blood information measuring apparatus of claim 4, further including a mode selector for switching between a normal mode and a special mode, wherein in the normal mode an observation image is produced from the image signal obtained under illumination of white light of a broad wavelength band and displayed on the monitor, and in the special mode the wavelength sets are applied to calculate the oxygen saturation level and the oxygen saturation level is displayed on the monitor.

11. The blood information measuring apparatus of claim 1, wherein the location detecting section performs image processing to an image of the internal body portion to detect the location of the internal body portion.

12. The blood information measuring apparatus of claim 1, wherein the wavelength sets include a superficial layer wavelength set having the types of the narrowband light selected from within a blue wavelength band of 400 nm to 500 nm and a middle layer wavelength set having the types of the narrowband light selected from within a green wavelength band of 500 nm to 600 nm, and the number of repetitions of the superficial layer wavelength set is set to two or more when the location detecting section detects that the internal body portion is in esophagus or large intestine, and the number of repetitions of the middle layer wavelength set is set to two or more when the location detecting section detects that the internal body portion is in stomach.

13. The blood information measuring apparatus of claim 12, wherein the wavelength sets include a deep layer wavelength set having the types of the narrowband light selected from within a red wavelength band of 600 nm to 1000 nm.

14. A blood information measuring method comprising the steps of:
applying illumination light to an internal body portion including a blood vessel;
receiving reflection light from the internal body portion illuminated with the illumination light, and outputting an image signal;
switching among wavelength bands of the illumination light to be applied to the internal body portion or of the reflection light such that two or more types of narrowband light constituting a designated wavelength set are applied or received successively, the two or more types of the narrowband light penetrating to similar depths into the internal body portion;
storing a wavelength set table in which the wavelength sets and the number of repetitions of the application of each wavelength set are stored, the number of repetitions of the application of at least one of the wavelength sets being two or more, and a combination of the number of repetitions of the application of each wavelength set being different according to a location of the internal body portion;
automatically and successively switching the designated wavelength set among the wavelength sets such that the application of the illumination light or the receipt of the reflection light of each of the wavelength sets is carried out for the number of repetitions stored in the wavelength table;
detecting a location of the internal body portion;
determining automatically the combination of the number of repetitions of application of each of the wavelength sets, based on the location detected, and
calculating blood information of blood in the blood vessel based on the image signal.

15. The blood information measuring method of claim 14, further including a step of displaying the blood information measured with the application of each of the wavelength set.

16. The blood information measuring method of claim 15, wherein the blood information is an oxygen saturation level of hemoglobin calculated based on absorbance.

* * * * *